US006111120A

United States Patent [19]

Myers

[11] Patent Number: 6,111,120

[45] Date of Patent: Aug. 29, 2000

[54] METHOD OF REFINING OILS AND FATS

[75] Inventor: Hyam Myers, Lane Cove, Australia

[73] Assignee: Hyam Myers Consulting Pty. Limited, South Wales, Australia

[21] Appl. No.: 09/011,275

[22] PCT Filed: Aug. 7, 1996

[86] PCT No.: PCT/AU96/00494

§ 371 Date: Feb. 10, 1998

§ 102(e) Date: Feb. 10, 1998

[87] PCT Pub. No.: WO97/07186

PCT Pub. Date: Feb. 27, 1997

[30] Foreign Application Priority Data

Aug. 11, 1995 [AU] Australia .................................... 4750

[51] Int. Cl.[7] .................................................. C07C 51/43

[52] U.S. Cl. ......................... 554/189; 554/175; 554/202; 554/207

[58] Field of Search .................................... 554/189, 175, 554/202, 207

[56] References Cited

U.S. PATENT DOCUMENTS 3,983,147 9/1976 Senda et al. ............................ 554/189

OTHER PUBLICATIONS

Derwent Soviet Inventions Illustrated, Section 1, Chemical, issued Sep. 1968, Petrochemicals, p. 1, SU 207310 (Shakhova et al.) Feb. 28, 1968.

Derwent Abstract Accession No. 84–026891, Class D23, E12, (E32), JP,A,58–217596 (Araki) Dec. 17, 1983.

*Primary Examiner*—Johann Richter
*Assistant Examiner*—J. Parsa
*Attorney, Agent, or Firm*—Wolf, Greenfield & Sacks, P.C.

[57] ABSTRACT

This invention relates to a new method of refining oils and fats. The method provides for the reduction of free fatty acids and/or soaps in oils and fats by mixing calcium oxide with said oils or fats.

8 Claims, No Drawings

METHOD OF REFINING OILS AND FATS

This application is a 371 of PCT/AU96/00494 filed on Aug. 7, 1996.

This invention relates to a new method for refining oils and fats. In particular it relates to a process for removing or separating free fatty acids (FFA) or residual soaps from oils and fats.

BACKGROUND

Free fatty acids and soaps may be present in many different types of fats and oils and generally it is desirable to remove or minimise the concentration thereof.

By the term "crude oil" as used herein we mean any oil that is obtained from seeds or other plant and animal matter. These oils may be produced by any known method. For example they may have been extracted from any known source of oil by any known mechanical or chemical extraction process.

When a crude oil or fat is produced by pressing, extraction, rendering or any other means it contains a variety of non-triglyceride impurities such as free fatty acids (FFA), phosphatides, sterols, pigments and hydrocarbons. Not all of these impurities are undesirable as in some instances they can impart important or preferred characteristics to the final oil product.

It is generally desirable, however, to remove or minimise the content of free fatty acids and soaps in the processed oil. Whilst the level of reduction of free fatty acids in the end product will vary depending on the desired use of the fat or oil, it is generally desirable to reduce the level of free fatty acids to less than 0.2%. Similarly it is generally desirable to reduce the level of soaps to less than 50 parts per million (ppm).

In most instances the free fatty acids are removed by the standard alkali refining process which includes the addition of caustic soda (NaOH) to the crude oil to form a largely oil insoluble sodium based soap which is then separated from the oil.

If soaps are present in an oil or fat they are generally removed by water washing to reduce the soap concentration to about 50 ppm then reduced further by treatment with a suitable bleaching earth or other adsorbent material.

The advantages of using caustic soda to remove free fatty acids include that it is readily available and it may also assist with the removal of other impurities such as phosphatides, carbohydrates and protein fragments. Further, it has been found that large quantities of oil can be refined with a high efficiency and minimum attention after the selection of: (a) preferred or optimum selection of the best method of separating the soap from the oil and (b) the optimum quantity and concentration of caustic soda.

The disadvantages of using caustic soda include that in general it is necessary to use a multi-step process to remove all the impurities and to handle the caustic materials. Further such an oil refining process produces a soap stock which is not environmentally friendly and requires further processing prior to disposal. Historically the soap stock was used in traditional soap processes, however, its disposal this way has decreased over recent years due to the greater use of detergents in preference to soaps. One solution for overcoming the disposal problem has been to further process the soap stock by acidulation to form free fatty acids which may be used as a high-energy ingredient in animal feeds or for chemical use. However, these further processes can be expensive and usually involve the use of other undesirable chemicals.

Attempts to effectively refine oils with other alkali materials such as calcium hydroxide and sodium carbonate have been tried. However, these compounds have not been proven to be as satisfactory as caustic soda and their use has been either abandoned or curtailed. For example, calcium hydroxide added as a "cream" to a crude oil requires several hours to reduce the FFA to about 0.2%. Sodium carbonate, on the other hand, does not possess the decolourising capacity of caustic soda but saponifies very little neutral oil.

It is also desirable in some instances to remove free fatty acids and/or soaps from, or minimise them in, fats and oils where the level of said free fatty acids or soaps have increased due to one or more chemical reactions such as during hydrogenation or esterification or frying. For example, the interest-erification of fats and oils may use an alkaline compound, notably sodium methoxide, to effect the randomisation. Water added at the completion of the reaction causes soap to be formed, these being usually removed by acidification and/or water washing.

In Russian Patent No. SU207310 it is reported that it is known to neutralise vegetable oils by treating them with magnesium oxide. This document teaches that this process can be improved by adding a dehydration agent to the oil with the magnesium oxide. The dehydration agent disclosed in this document is gypsum. However, this process has not been widely used and it does not result in the removal of the free fatty acids to commercially acceptable levels. This document also does not suggest or teach that any other alkali metal oxide could be used in an oil or fat refining process.

It is an object of the present invention to develop a method for refining oils and fats to reduce the level of free fatty acids or soaps from the oils or fats in an economical and environmentally friendly way.

SUMMARY OF THE INVENTION

According to a first aspect of the invention there is provided a method of refining an oil or fat to reduce the level of free fatty acids and/or soaps in the oil or fat, wherein said method includes mixing calcium oxide with said oils or fats.

Applicant has found that this process removes substantially all of the free fatty acids and/or soaps in the oil or fat and forms environmentally friendly soaps which are insoluble in the oil or fat. The level of free fatty acids and soaps remaining in the oil or fat after the method of the invention will depend on the type of free fatty acids or soaps which are present and need to be removed. However, it in general reduces the level of free fatty acids to less than 0.2% and the level of soaps to less than 50 ppm.

The calcium oxide may be added to the oil or fat in any suitable form. The calcium oxide may be added in a granular or powder form or in the form of a solution or as a mixture of various forms. The selection of the form of the calcium oxide will depend upon the physical parameters of the reaction site and the desired reaction kinetics.

The calcium oxide may be provided from any known source. Preferred sources of calcium oxide are high calcium quicklime and dolomite quicklime.

Some of the advantages of selecting calcium oxide are that it is readily available and the calcium soaps produced by the method of the invention are environmentally friendly and may be used as direct additives for other products such as animal food products. A further advantage of adding calcium oxide is that it allows for the development and implementation of an essentially dry refining process (hereinafter referred to as DRP), which utilises relatively economical and environment friendly reactants as compared to those used in traditional processes for removing free fatty acids from oils and fats.

In a preferred embodiment of the invention other materials may also be added which may assist with the ability of the calcium oxide to remove or minimise the level of free fatty acids. For example, any suitable alkali metal or ammonium compound may be added to the oil or fat with the calcium oxide. The alkali metal compound may be any suitable hydroxide, oxide or salt of the alkali metal. Examples of suitable alkali metal or ammonium compounds include sodium hydroxide, potassium hydroxide, ammonium hydroxide or any other hydroxide of the alkali metals of Group 1 of the periodic table. A further embodiment of the invention permits the use of water soluble inorganic and organic salts of either ammonia or alkali metals which can react with the calcium oxide to form hydroxides. Examples of these compounds are sodium sulphate, sodium carbonate, sodium orthophospate, sodium metasilicate, sodium lauryl sulphate and sodium oxalate.

In a particularly preferred embodiment of the process of the invention sodium hydroxide (caustic soda) is added to the oil or fat with the calcium oxide. Any suitable amount of caustic soda may be added. It has been found, however, that it is not necessary to add such quantities of caustic soda as would be required in a traditional alkali refining method.

The alkali metal or ammonium compound may be added to the oil or fat in any suitable form. The alkali metal or ammonium compound may be added in a granular or powder form. Preferably the alkali metal or ammonium compound is added in the form of an aqueous solution.

In a preferred embodiment of the invention the calcium oxide and alkali metal or ammonium compound may be added to the oil or fat in any particular order. Alternatively the calcium oxide and alkali metal or ammonium compound may be added simultaneously.

In a preferred embodiment of the invention it is desirable to mix in additional water with the fat or oil. The water may be added either before or after the addition of the metal oxide and alkali earth compound.

Ideally the reaction conditions for the method of the invention are selected to reduce the presence of the free fatty acids and soaps in the oil or fat. These reaction conditions include the selection of reaction temperature and time to reduce or minimise the level of residual free fatty acids in the oil or fat.

Whilst not wishing to be bound to any particular theory it has been postulated that the various reactions taking place to remove the free fatty acids are as follows:

1. $CaO + 2RCOOH \longrightarrow (RCOO)_2Ca + H_2O$

2. $CaO + H_2O \longrightarrow Ca(OH)_2$

In the embodiment of the invention where sodium hydroxide is also added to the oil, it has been postulated that the various reactions taking place may be as follows:

1. $NaOH + RCOOH \longrightarrow RCOONa + H_2O$

2. $2RCOONa + CaO + H_2O \longrightarrow (RCOO)_2Ca + 2NaOH$

3. $CaO + H_2O \longrightarrow Ca(OH)_2$

4. $CaO + NaOH \longrightarrow CaO.NaOH$

It is also important to note that the object of the invention is to reduce the level of free fatty acids and soaps in the oils or fat. Thus additional processing either before or after the method of the invention may be undertaken to remove other impurities from the said oil or fat. For example, removal of phospholipids and minor contaminants may require implementing either one or more other known degumming or bleaching processes.

In order to assist in arriving at an understanding of the present invention, some preferred embodiments of the invention are illustrated in the following examples. However, it should be understood that the following description is illustrative only and should not be taken in any way as a restriction on the generality of the invention as described above.

In the examples determinations of the level of Free Fatty Acids are referred to. In these examples the level of Free Fatty Acids (FFA) is determined by AOCS Method Ca 5a -40. The determinations were conducted by placing a sample in 95% ethanol and titrating with 0.1N NaOH, and using phenolphthalein as the indicator. The % FFA was calculated by the formula % FFA=V×56×0.05/W where V=titration, W=sample weight. Soap determinations were by AOCS method Cc17-79.

EXAMPLE 1

A sample of cold pressed canola oil was obtained. Commercial grade Stearic Acid was added to this oil to achieve an oil sample with a level of 1.2% free fatty acids (FFA).

100 ml of the canola oil with 1.2% FFA was heated to about 80° C. and 0.3 gm of quicklime was added and stirred thoroughly for about five minutes. The mixture was filtered to obtain a clear oil.

The level of FFA in the resulting clear oil was determined to be 0.16%.

EXAMPLE 2

A second sample of canola oil having 1.2% FFA was prepared by the same method as described for example 2.

100 ml of the canola oil with 1.2% FFA was heated to about 80° C. and 0.2 ml of 25% NaOH was subsequently added and stirred for about one minute. Immediately following this 1.0 gm of quicklime was added to the mixture and stirred for about another five minutes. 0.2 gm of filter aid was added to the mixture which was then filtered to obtain a clear oil.

The level of FFA in the resulting clear oil was determined to be 0.025%.

EXAMPLE 3

A 100 ml sample of sunflower oil containing about 10% by weight of meal fines (foots) and having a FFA of 0.37% was obtained.

This sample was heated to about 80° C. and 0.2 ml of 25% NaOH was added and stirred for about 1 minute. Immediately following this 0.7 gm of quicklime was added and stirred for about another 5 minutes. 0.2 gm of filter aid was added to the mixture which was then filtered to obtain a clear oil.

The level of FFA in the resulting clear oil was determined to be 0.06%.

EXAMPLE 4

To 100 gm crude sunflower oil was added 0.3 gm quicklime. The mixture was shaken for 1 minute then 0.3 ml 15% w/w solution of ammonium sulphate was added. The mass was then shaken intermittently for 20 minutes at room temperature, allowed to stand for 30 minutes, heated to about 60° C. then filtered to obtain a clear oil.

The level of FFA in the resulting oil was 0.18%.

The above trial was repeated but 0.3 ml of water added after 20 minutes of shaking and after heating the mass to about 60° C. The water was mixed in for 5 minutes before filtration.

The level of FFA in the resulting oil was 0.05%.

EXAMPLE 5

A sample of refined, bleached and deodorised canola oil was obtained. A commercial grade of stearic acid and the calculated quantity of 25% caustic soda were added to provide a soap concentration of 1200 ppm.

To 100 gm of this oil was added 0.18 gm CaO, calculated to react with both the sodium soap and the water. The mass was stirred for 5 minutes at room temperature, 0.5 gm filter aid added and the mixture filtered to obtain a clear oil.

The resulting oil had a soap content of 38 ppm. Those skilled in the art will appreciate that there may be many variations and modifications of the examples of the processes described herein which are within the scope of the present invention.

What is claimed is:

1. A method, for refining oil or fat comprising:

providing an oil or fat having a level of free fatty acids;

precipitating at least a portion of the free fatty acids from the oil or fat by adding calcium oxide to the oil or fat;

wherein the oil or fat comprises an esterified mixture of glycerol and free fatty acids.

2. A method according to claim 1, wherein the source of calcium oxide is selected from high calcium quicklime or dolomitic quicklime.

3. A method according to claim 2, wherein the level of free fatty acids is reduced to less than 0.2%.

4. A method according to claim 3, wherein the oil or fat includes a level of soaps, and further comprising reducing the level of soaps to less than 50 ppm.

5. A method according to claim 4, further comprising catalyzing the precipitation of the free fatty acids by adding a catalyst to the oil or fat.

6. A method according to claim 5, wherein the catalyst is an alkali metal or ammonium compound.

7. A method according to claim 6, wherein the alkali metal or ammonium compound is selected from the group consisting of sodium hydroxide, potassium hydroxide, ammonium hydroxide, ammonium sulphate, sodium sulphate, sodium carbonate, sodium orthophosphate, sodium metasilicate, sodium lauryl sulphate, sodium oxalate, and mixtures thereof.

8. A method according to claim 1, further comprising adding water to the oil or fat.

* * * * *